United States Patent
O'Lenick

(10) Patent No.: US 10,246,552 B1
(45) Date of Patent: Apr. 2, 2019

(54) PHOTOSTABILIZING POLYMER

(71) Applicant: Thomas O'Lenick, Dacula, GA (US)

(72) Inventor: Thomas O'Lenick, Dacula, GA (US)

(73) Assignee: SurfTech Corporation, Lawrenville, GA (US)

( * ) Notice: Subject to any disclaimer, the term of this patent is extended or adjusted under 35 U.S.C. 154(b) by 0 days.

(21) Appl. No.: 15/648,827

(22) Filed: Jul. 13, 2017

Related U.S. Application Data

(60) Provisional application No. 62/361,653, filed on Jul. 13, 2016.

(51) Int. Cl.
*C08G 63/685* (2006.01)
*A61Q 17/04* (2006.01)
*A61K 8/85* (2006.01)

(52) U.S. Cl.
CPC ............ *C08G 63/6856* (2013.01); *A61K 8/85* (2013.01); *A61Q 17/04* (2013.01); *C08G 63/6858* (2013.01); *A61K 2800/52* (2013.01)

(58) Field of Classification Search
None
See application file for complete search history.

(56) References Cited

U.S. PATENT DOCUMENTS

2014/0004060 A1* 1/2014 Levins ............... C08G 63/6856
424/59

* cited by examiner

*Primary Examiner* — Alicia L Otton

(57) ABSTRACT

The present invention is directed to a series of polymers containing end groups that are absorb ultraviolet (UV) light. The invention is also to the use of such compounds in the cosmetic, toiletry and personal care areas. These polymers can be utilized to produce films and provide solvent properties for the formulation of for ultra-violet absorbing formulations (like sunscreens) and provide outstanding dispensability and anti-agglomeration properties for inorganic sunscreens containing ZnO and $TiO_2$. The ability to provide uniform non agglomerating sun care formulations results in formulations with increase SPF values and improved "water-resistant" properties in cosmetic formulation. The compounds of the present invention by themselves do not have ultra violet absorption at the particular wavelength that contributes to sun protection and consequently are not themselves sunscreens.

19 Claims, No Drawings

PHOTOSTABILIZING POLYMER

RELATED APPLICATIONS

This application claims priority from U.S. provisional application Ser. No. 62/361,653 filed on Jul. 13, 2016, which is hereby incorporated by reference in its entirety.

GOVERNMENT SPONSORSHIP

None

FIELD OF INVENTION

The present invention is directed to a series of polymers containing end groups that are absorb ultraviolet (UV) light. The invention is also to the use of such compounds in the cosmetic, toiletry and personal care areas. These polymers can be utilized to produce films and provide solvent properties for the formulation of for ultra-violet absorbing formulations (like sunscreens) and provide outstanding dispensability and anti-agglomeration properties for inorganic sunscreens containing ZnO and $TiO_2$. The ability to provide uniform non-agglomerating sun care formulations results in formulations with increased SPF values and improved "water-resistant" properties in cosmetic formulation. The compounds of the present invention by themselves do not have ultra violet absorption at the particular wavelength that contributes to sun protection and consequently are not themselves sunscreens.

BACKGROUND OF THE INVENTION

The harmful effects of solar radiation can have a huge negative impact on humans. Commercial sunscreens contain "filters" that, in the organic filters case, absorb ultraviolet light. When a molecule absorbs light, the absorbed photon can excite an electron from a low energy (bonding) orbital to a higher energy orbital (non-bonding). The "excited" electron has to release energy to return to the ground state. There are several pathways for this electron to release energy to return to its ground state: fluorescence, thermal, and chemical reactions to list a few. It is important in cosmetic sunscreens that the organic filters (i.e. the molecules that absorb UV at specified wavelengths) are returned to their ground state as quickly as possible and without chemical modification. One of the more efficient ways to achieve this in a commercial product is to include "Photostabilizers" that can "absorb" the energy of the excited electrons.

U.S. Pat. No. 9,145,383 to Bonda teaches conjugated fused polycyclic molecules that quench, dissipate, and/or otherwise resolve excited state energy, normally by way of releasing it as heat. The current invention uses a similar mechanism as described by Bonda, but has the added benefit of being a polymeric material capable of forming a very water-resistant film.

Esters of salicylic acid have been used as sunscreens and also have been prepared and used primarily as defoliating agents for the skin and conditioning agents for hair. Esters synthesized from longer chain di-acids, such as azelic, adipic, or maleic acid tend to yield esters with good low temperature characteristics. The esters of this type seem to have a "heavy" aesthetic. The esterification of these di-acids with a low molecular weight branched alcohols have produced esters with less "heavy" sticky aesthetic.

Esters of dimer acids or dimer alcohol are primarily known for their anti-irritating characteristics when employed in a formulation, however the aesthetics of these esters are much heavier than desired in most formulation.

Esters derived from benzoic acid, have been prepared and been used as sunscreen synergists as well as defoliants for the skin. The properties of these esters arise from the aromatic nature of the benzoic acid starting material. The esterification of benzoic acid does not affect the aromatic nature of the starting material or monomer, thus making esters and polymeric species of these materials attractive in the cosmetic industry.

All of the esters above have been used in the cosmetic industry to maximize performance in a formulation. Surprising and unexpectedly, we have found that the specific polyesters of the present invention, possesses the highly desirable cosmetic properties including but not limited to skin feel, film formation and conditioning benefits.

An additional aspect of the present invention comes from the presence of aromatic groups in these polyesters. The aromatic groups allow for significant improvement of the sun protection factor, while in and of themselves not being sunscreen actives. Put another way, all aromatic compounds have a wavelength in which they absorb ultraviolet radiation. However, only some classified as sunscreen actives absorb in either the UVA or UVB wavelengths. It is compounds that absorb in the non-UVA, UVB that are useful in the present invention.

OBJECT OF THE INVENTION

The present invention is directed toward a series of polymers that have a photo-absorbing group. They are synthesized by reaction (1) a diacid (2) a diol, and (3) a monofunctional alcohol that absorbs ultraviolet light. The end-capping allows for precise control of the molecular weight, change in aesthetics and control of how much chromophore is incorporated into the polymer.

SUMMARY OF THE INVENTION

The present invention is related to a series of novel photo-absorbing polymers that are synthesized by the reaction of (1) a diacid (2) a diol, and (3) a monofunctional alcohol that absorbs ultraviolet light. This photo-absorbing end group has a dual purpose in this polymerization: (a) mono-functional monomers are commonly used to control molecular weight of a polymer chain and are often referred to as chain terminators. Once a chain terminator reacts, it "caps" the polymer chain, this allows for control of aesthetics of the polymer chain. (b) Chain terminators, being mono-functional, always terminate the polymer chain. We have determined that capping the polymer with these groups is far more efficient that placing the groups on non-terminal groups.

By the term photo-absorbing is meant: an aromatic group having an absorbance in the 300-400 nm ultraviolet range. This photo-absorbing group provides the ability of the polymers of the current invention to form a film and help photostabilize organic filters, specifically avobenzone.

The diacid and diol used in the polymerization process allows for control of the polymers performance in formulation. Longer alkyl chain diacids can lead to a polymer with a higher melting point. This can lead to a "butter-like" affect when used in formulation. The choice of a small (lower molecular weight) diacid will lead to a higher molecular weight more honey-like polymer will be the result. The ability to prepare products that have a range of aesthetics when applied to the skin, answer a long felt need to replace the sticky feel provided by polymers that are made by free radical polymerization. In addition these polymers do not have residual free radical monomers, since they are not made by free radical processes. Free radical monomers are highly undesirable in cosmetic formulations.

DETAILED DESCRIPTION OF THE INVENTION

One aspect of the present invention is directed towards a photostabilizing polymer prepared by the esterification reaction of:

1. An photo-absorbing group having the following structure:

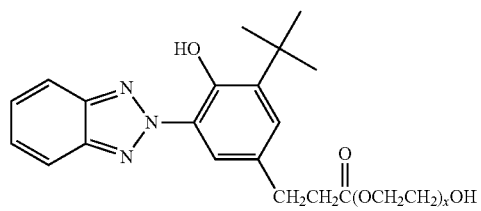

wherein;
x is an integer ranging from 1 to 10.
2. A diacid independently selected from the groups consisting of:
a. A fatty acid having to the following structure:

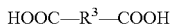

wherein;
$R^3$ is alkyl containing 2 to 12 carbon atoms;
b. Dimer Acid;
c. Hydrogenated Dimer Acid;
and mixtures thereof;
3. A diol having the following structure:

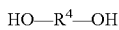

wherein;
$R^4$ is an integer ranging from 3 to 12 carbons;
4. A monofunctional alcohol independently selected from the groups consisting of:
a. a branched alkyl having the structure:

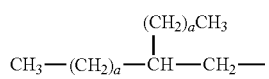

wherein;
a is an integer ranging from 3-15;
b is an integer ranging from 5-17;
and mixtures thereof;
b. A fatty alcohol having the structure:

wherein;
$R^2$ is alkyl having 8 to 26 carbon atoms,
and mixtures thereof.

Another aspect of the present invention is directed towards a process of protecting skin, which comprises contacting the skin with a photostabilizing concentration of a photostabilizing polymer prepared by the esterification reaction of:

1. An photo-absorbing group having the following structure:

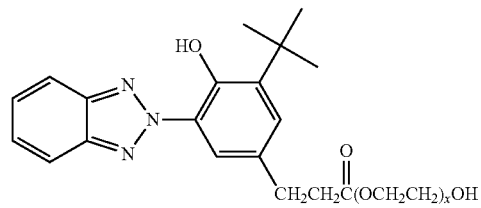

wherein;
x is an integer ranging from 1 to 10.
2. A diacid independently selected from the groups consisting of:
a. A fatty acid having to the following structure:

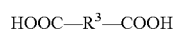

wherein;
$R^3$ is alkyl containing 2 to 12 carbon atoms;
b. Dimer Acid;
c. Hydrogenated Dimer Acid;
and mixtures thereof;
3. A diol having the following structure:

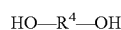

wherein;
$R^4$ is an integer ranging from 3 to 12 carbons;
4. A monofunctional alcohol independently selected from the groups consisting of:
a. a branched alkyl having the structure:

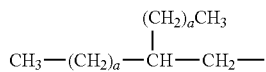

wherein;
a is an integer ranging from 3-15;
b is an integer ranging from 5-17;
and mixtures thereof;
b. A fatty alcohol having the structure:

wherein;
$R^2$ is alkyl having 8 to 26 carbon atoms,
and mixtures thereof.

PREFERRED EMBODIMENTS

In a preferred embodiment the photo-absorbing group has the following structure:

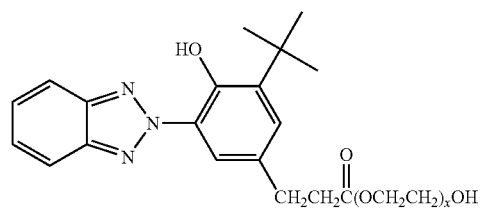

wherein x is 6.

In a preferred embodiment the photo-absorbing group has the following structure:

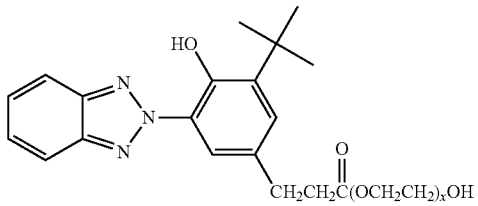

wherein x is 7.

In a preferred embodiment the diol is propanediol.

In a preferred embodiment the diacid is hydrogenated dimer acid.

In a preferred embodiment the diacid is azelic acid.

In a preferred embodiment the photo-absorbing group has the following structure:

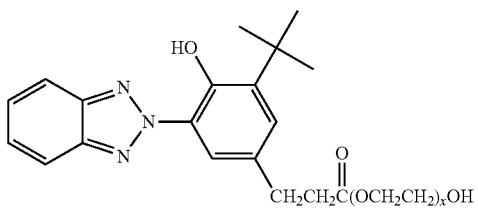

wherein x is 6 and the diacid is dimer acid.

In a preferred embodiment the photo-absorbing group has the following structure:

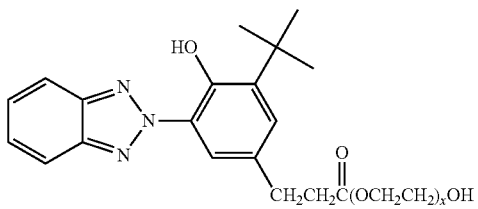

wherein x is 7 and the diacid is dimer acid.

In a preferred embodiment the diol is propanediol.

In a preferred embodiment the diacid is hydrogenated dimer acid.

In a preferred embodiment the diacid is azelic acid.

In a preferred embodiment the photostabilizing concentration is between 0.1 and 10.0% by weight.

In another preferred embodiment the photostabilizing concentration is between 0.5 and 5.0% by weight.

In another preferred embodiment the photostabilizing concentration is between 1.0 and 3.0% by weight.

EXAMPLES

Raw Materials

Photo-Absorbing Group

Photo-absorbing agents are commercially available from a variety of sources including Mayzo, Inc. of Suwannee, Ga. It has the following structure:

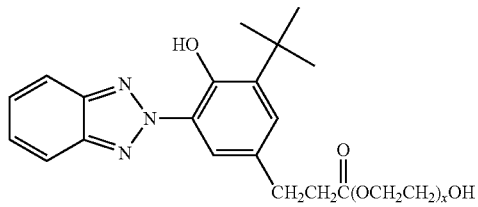

The CAS number is 104810-48-2.

| Example | x | MW |
|---------|----|-----|
| 1 | 2 | 383 |
| 2 | 6 | 603 |
| 3 | 7 | 647 |
| 4 | 10 | 779 |

Dicarboxylic Acids

Dicarboxylic acids are useful raw materials in the synthesis of the compounds of the present invention and are commercially available from a variety of sources including Cognis. They have the following structure:

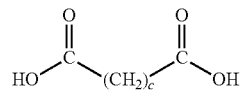

| Saturated Dicarboxylic acids | | | |
|---------|-------------|----|------------------|
| Example | Common Name | c | Molecular Weight |
| 5 | Malonic | 1 | 104 |
| 6 | Succinic | 2 | 118 |
| 7 | Glutaric | 3 | 132 |
| 8 | Adipic | 4 | 146 |
| 9 | Pimelic | 5 | 160 |
| 10 | Subric | 6 | 174 |
| 11 | Azelaic | 7 | 188 |
| 12 | Sebacic | 8 | 202 |
| 13 | Undecanedioic | 9 | 216 |
| 14 | Dodecanedioic | 10 | 230 |

Example 15 Dimer Acid

Dimer acid is an item of commerce available commercially from Cognis Corporation. It conforms to the following structure:

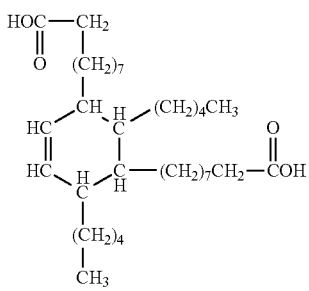

Example 16 Hydrogenated Dimer Acid

Hydrogenated dimer acid is an item of commerce available commercially from Henkel Corporation. It conforms to the following structure:

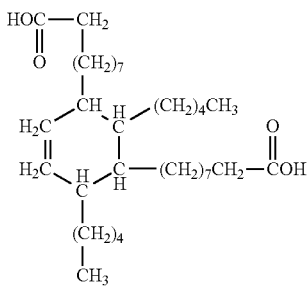

Fatty Alcohols Names

Fatty alcohols are useful as raw materials in the synthesis of the compounds of the present invention are commercially available from a variety of sources including BASF. They conform to the following structure;

R—OH

| Example | Formula | Name | Molecular Weight |
|---|---|---|---|
| 17 | $C_8H_{18}O$ | 1-Capryl | 130.0 |
| 18 | $C_9H_{20}O$ | 1-Nonanol | 144.3 |
| 19 | $C_{10}H_{22}O$ | 1-Decanol | 158.3 |
| 20 | $C_{11}H_{24}O$ | Undecanol | 172.3 |
| 21 | $C_{12}H_{26}O$ | Dodecanol | 186.3 |
| 22 | $C_{18}H_{38}O$ | Stearyl | 270.5 |
| 23 | $C_{22}H_{46}O$ | Behenyl | 326.6 |

Guerbet Alcohols

Guerbet alcohols useful as raw materials in the preparation of compounds of the present invention are commercially available from a variety of sources including Sasol North America Incorporated of Houston Tex.

The structures are well known to those skilled in the art.

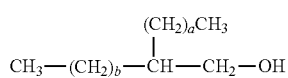

| Example | A | b | Molecular Weight |
|---|---|---|---|
| 24 | 15 | 17 | 466.0 |
| 25 | 13 | 11 | 410.0 |
| 26 | 9 | 7 | 298.0 |

Diols

Diols are useful as raw materials in the synthesis of the compounds of the present invention are commercially available from a variety of sources including BASF. They conform to the following structure;

$HO(CH_2)_cOH$

| Example | Formula | Name | Molecular Weight |
|---|---|---|---|
| 27 | $HO(CH_2)_3OH$ | 1,3-Propanediol | 74.0 |
| 28 | $HO(CH_2)_{10}OH$ | 1,10-Decandiol | 174.3 |
| 29 | $HO(CH_2)_{12}OH$ | 1,12-Dodecanediol | 202.3 |

Preparation of the Photo-Absorbing Polymer

Photo-Absorbing Terminated Polymer

General Procedure

To a flask equipped with thermometer, heat and distillation ability is added the specified number of grams of chain terminator (examples 1-4), diacid (examples 6-16) and the specified number of grams of the specified a diol (examples 27-29). The mixture is heated to 160-200° C. under agitation. The temperature is held in this range for 8-10 hours as water distills off. The resulting product is cooled and used without additional purification.

| | Photo-absorbing | | Diacid | | Diol | | |
|---|---|---|---|---|---|---|---|
| Example | Example | Grams | Example | Grams | Example | Grams | DP |
| 30 | 1 | 82.25 | 6 | 46.08 | 27 | 21.67 | 3 |
| 31 | 1 | 47.35 | 9 | 53.95 | 28 | 48.70 | 5 |
| 32 | 1 | 25.62 | 11 | 62.87 | 29 | 61.51 | 10 |
| 33 | 1 | 63.69 | 14 | 69.54 | 27 | 16.78 | 5 |
| 34 | 1 | 23.83 | 15 | 101.66 | 28 | 24.51 | 4 |
| 35 | 1 | 13.34 | 16 | 104.64 | 29 | 32.02 | 10 |
| 36 | 2 | 98.48 | 6 | 35.04 | 27 | 16.48 | 3 |
| 37 | 2 | 63.11 | 9 | 45.67 | 28 | 41.22 | 4 |
| 38 | 2 | 36.73 | 11 | 57.26 | 29 | 56.01 | 10 |
| 39 | 2 | 80.61 | 14 | 55.90 | 27 | 13.49 | 3 |
| 40 | 2 | 34.39 | 15 | 93.16 | 28 | 22.46 | 5 |
| 41 | 2 | 19.98 | 16 | 99.56 | 29 | 30.47 | 10 |
| 42 | 3 | 100.84 | 6 | 33.44 | 27 | 15.73 | 3 |
| 43 | 3 | 65.70 | 9 | 44.31 | 28 | 39.99 | 5 |
| 44 | 3 | 38.72 | 11 | 56.25 | 29 | 55.03 | 10 |
| 45 | 3 | 83.23 | 14 | 53.79 | 27 | 12.98 | 3 |
| 46 | 3 | 36.29 | 15 | 91.62 | 28 | 22.09 | 5 |
| 47 | 3 | 21.23 | 16 | 98.60 | 29 | 30.17 | 10 |
| 48 | 4 | 106.77 | 6 | 29.40 | 27 | 13.83 | 3 |
| 49 | 4 | 72.61 | 9 | 40.67 | 28 | 36.71 | 5 |
| 50 | 4 | 44.29 | 11 | 53.44 | 29 | 52.28 | 10 |
| 51 | 4 | 90.02 | 14 | 48.32 | 27 | 11.66 | 3 |
| 52 | 4 | 41.64 | 15 | 87.31 | 28 | 21.05 | 5 |
| 53 | 4 | 24.84 | 16 | 95.83 | 29 | 29.33 | 10 |
| 54 | 2 | 50.34 | 16 | 91.22 | 27 | 8.44 | 3 |
| 55 | 2 | 37.52 | 16 | 102.00 | 27 | 10.48 | 5 |
| 56 | 2 | 22.93 | 16 | 114.26 | 27 | 12.81 | 10 |

Mono-Terminated Photo-Absorbing Polymers

General Procedure

To a flask equipped with thermometer, heat and distillation ability is added the specified number of grams of chain terminator (examples 1-4), diacid (examples 6-16), diol (examples 27-29), and the specified number of grams of the monofunctional alcohol (examples 17-26). The mixture is heated to 160-200° C. under agitation. The temperature is held in this range for 8-10 hours as water distills off. The resulting product is cooled and used without additional purification.

| | Photo-absorbing | | Diacid | | Diol | | Monoalcohol | | |
|---|---|---|---|---|---|---|---|---|---|
| Example | Example | Grains | Example | Grains | Example | Grains | Example | Grains | DP |
| 57 | 1 | 50.22 | 6 | 56.27 | 27 | 17.05 | 17 | 26.46 | 3 |
| 58 | 1 | 24.83 | 9 | 56.57 | 28 | 17.53 | 22 | 51.06 | 5 |
| 59 | 1 | 12.97 | 11 | 63.68 | 29 | 11.06 | 23 | 62.29 | 10 |
| 60 | 1 | 30.44 | 14 | 66.48 | 27 | 37.04 | 24 | 16.04 | 3 |
| 61 | 1 | 11.85 | 15 | 101.09 | 28 | 12.69 | 25 | 24.37 | 5 |
| 62 | 1 | 6.73 | 16 | 105.68 | 29 | 5.24 | 26 | 32.34 | 10 |
| 63 | 2 | 66.32 | 6 | 47.19 | 27 | 14.30 | 17 | 22.20 | 3 |
| 64 | 2 | 35.70 | 9 | 51.66 | 28 | 16.01 | 22 | 46.63 | 5 |
| 65 | 2 | 19.46 | 11 | 60.66 | 29 | 10.54 | 23 | 59.34 | 10 |
| 66 | 2 | 42.92 | 14 | 59.54 | 27 | 33.17 | 24 | 14.37 | 3 |
| 67 | 2 | 17.85 | 15 | 96.70 | 28 | 12.13 | 25 | 23.31 | 5 |
| 68 | 2 | 10.34 | 16 | 103.03 | 29 | 5.11 | 26 | 31.53 | 10 |
| 69 | 3 | 68.93 | 6 | 45.72 | 27 | 13.85 | 17 | 21.50 | 3 |
| 70 | 3 | 37.65 | 9 | 50.78 | 28 | 15.74 | 22 | 45.83 | 5 |
| 71 | 3 | 20.68 | 11 | 60.09 | 29 | 10.44 | 23 | 58.79 | 10 |
| 72 | 3 | 45.11 | 14 | 58.32 | 27 | 32.49 | 24 | 14.07 | 3 |
| 73 | 3 | 18.98 | 15 | 95.87 | 28 | 12.03 | 25 | 23.11 | 5 |
| 74 | 3 | 11.04 | 16 | 102.51 | 29 | 5.08 | 26 | 31.37 | 10 |
| 75 | 4 | 78.88 | 6 | 41.80 | 27 | 12.66 | 17 | 19.66 | 3 |
| 76 | 4 | 43.12 | 9 | 48.31 | 28 | 14.97 | 22 | 43.60 | 5 |
| 77 | 4 | 24.22 | 11 | 58.45 | 29 | 10.15 | 23 | 57.18 | 10 |
| 78 | 4 | 51.18 | 14 | 54.95 | 27 | 30.62 | 24 | 13.26 | 3 |
| 79 | 4 | 22.28 | 15 | 93.46 | 28 | 11.73 | 25 | 22.53 | 5 |
| 80 | 4 | 13.09 | 16 | 101.00 | 29 | 5.01 | 26 | 30.91 | 10 |
| 81 | 2 | 27.51 | 16 | 99.69 | 27 | 13.59 | 26 | 9.21 | 3 |
| 82 | 2 | 20.03 | 16 | 108.90 | 27 | 9.90 | 26 | 11.17 | 5 |
| 83 | 2 | 11.93 | 16 | 118.87 | 27 | 5.89 | 26 | 13.31 | 10 |

What is claimed:

1. A photostabilizing polymer prepared by the esterification reaction of:
   1. a photo-absorbing group having the following structure:

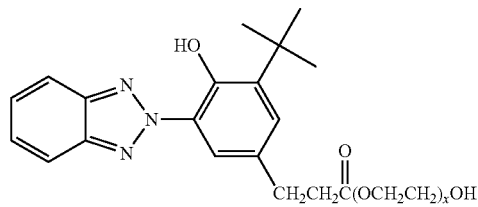

wherein;
   x is an integer ranging from 1 to 10;
   2. a diacid independently selected from the group consisting of:
      a. a fatty acid having to the following structure:

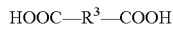

wherein;
      $R^3$ is alkyl containing 2 to 12 carbon atoms;
      b. dimer Acid;
      c. hydrogenated dimer acid;
      d. mixtures thereof;
   and
   3. a diol having the following structure:

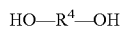

wherein;
   $R^4$ is alkyl ranging from 3 to 12 carbons; and
   4. a monofunctional alcohol independently selected from the group consisting of:
      a. a branched alkyl having the structure:

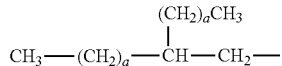

wherein;
      a is an integer ranging from 3-15;
      b is an integer ranging from 5-17;
      and mixtures thereof;
      b. a fatty alcohol having the structure:

wherein;
      $R^2$ is alkyl having 8 to 26 carbon atoms,
      and mixtures thereof.

2. The photostabilizing polymer of claim 1 wherein the photo-absorbing group has the following structure:

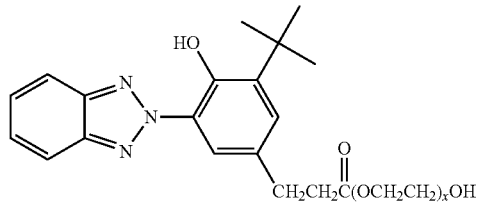

wherein x is 6.

1. a photo-absorbing group having the following structure:

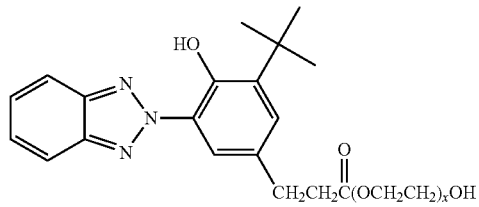

wherein;
x is an integer ranging from 1 to 10;
2. a diacid independently selected from the groups consisting of:
  a. A fatty acid having to the following structure:

HOOC—R³—COOH wherein;
  R³ is alkyl containing 2 to 12 carbon atoms;
  b. dimer Acid;
  c. hydrogenated dimer acid;
and mixtures thereof;
3. a diol having the following structure:

HO—R⁴—OH wherein;
  R⁴ is alkyl moiety having from 3 to 12 carbons; and
4. a monofunctional alcohol independently selected from the group consisting of:
  a. a branched alkyl having the structure:

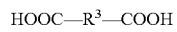

wherein;
  a is an integer ranging from 3-15;
  b is an integer ranging from 5-17;
  and mixtures thereof;
  b. a fatty alcohol having the structure:

R²—OH wherein;
  R² is alkyl having 8 to 26 carbon atoms,
  and mixtures thereof.

13. The process of claim 12 wherein the photostabilizing concentration is between 0.1 and 10.0% by weight.

14. The process of claim 12 wherein the photostabilizing concentration is between 0.5 and 5.0% by weight.

15. The process of claim 12 wherein the photo-absorbing group has the following structure:

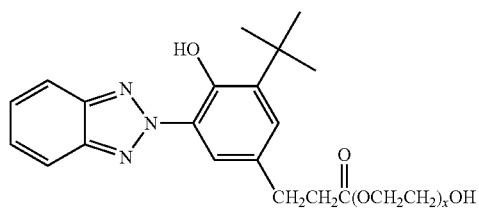

wherein x is 6.

3. The photostabilizing polymer of claim 1 wherein the photo-absorbing group has the following structure:

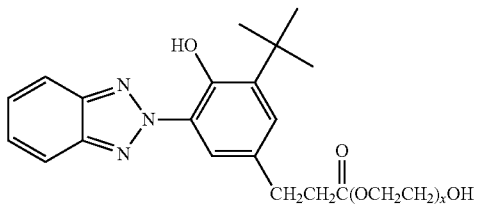

wherein x is 7.

4. The photostabilizing polymer of claim 1 wherein the diol is propanediol.

5. The photostabilizing polymer of claim 1 wherein the diacid is hydrogenated dimer acid.

6. The photostabilizing polymer of claim 1 wherein the diacid is azelic acid.

7. The photostabilizing polymer of claim 1 wherein the photo-absorbing group has the following structure:

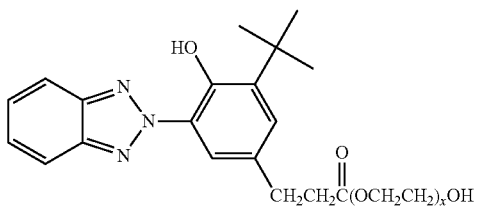

wherein x is 6 and the diacid is dimer acid.

8. The photostabilizing polymer of claim 1 wherein the photo-absorbing group has the following structure:

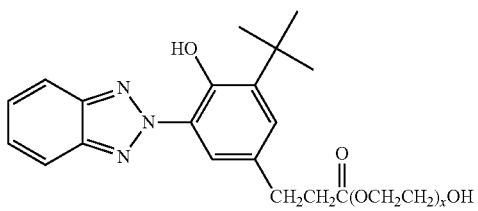

wherein x is 7 and the diacid is dimer acid.

9. The photostabilizing polymer of claim 2 wherein the diol is propanediol.

10. The photostabilizing polymer of claim 2 wherein diacid is hydrogenated dimer acid.

11. The photostabilizing polymer of claim 2 wherein the diacid is azelic acid.

12. A process of protecting skin, which comprises contacting the skin with a photostabilizing concentration of a photostabilizing polymer prepared by the esterification reaction of:

16. The process of claim 12 wherein the photo-absorbing group has the following structure:
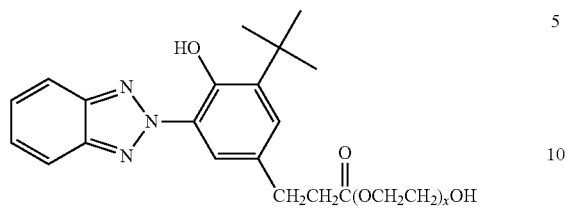
wherein x is 7.
17. The process of claim 12 wherein the diol is propanediol.
18. The process of claim 12 wherein the diacid is hydrogenated dimer acid.
19. The process of claim 12 wherein the diacid is azelic acid.
* * * * *